United States Patent
Henegar et al.

(10) Patent No.: US 6,376,711 B1
(45) Date of Patent: Apr. 23, 2002

(54) METHOD FOR THE PREPARATION OF ARYL ETHERS

(75) Inventors: Kevin E. Henegar, Portage; Sarah E. Mancini, Kalamazoo; Keith D. Maisto, Portage, all of MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/469,429

(22) Filed: Dec. 23, 1999

Related U.S. Application Data

(60) Provisional application No. 60/114,092, filed on Dec. 29, 1998.

(51) Int. Cl.[7] .............................................. C07C 213/00
(52) U.S. Cl. ........................ 564/349; 564/351; 544/174
(58) Field of Search ................................ 564/349, 351; 544/174

(56) References Cited

U.S. PATENT DOCUMENTS

| 4,229,449 A | 10/1980 | Melloni et al. ........ 424/248.58 |
| 5,068,433 A | 11/1991 | Melloni et al. ............. 564/349 |
| 5,391,735 A | 2/1995 | Melloni et al. ............. 544/174 |

OTHER PUBLICATIONS

Cossy, J., et al., "Silylation Selection Par L Hexamethyldisilazane", *Tetrahedron Letters*, vol. 28, No. 48, XP–002136947, 6039–6040, (1987).

*Primary Examiner*—Samuel Barts
(74) *Attorney, Agent, or Firm*—Schwegman, Lundberg, Woessner & Kluth, P.A.

(57) ABSTRACT

The invention relates to a method for preparing aryl ethers that are useful as antidepressants. The invention also relates to intermediates useful in the method and to methods for preparing such intermediates.

9 Claims, 4 Drawing Sheets

METHOD FOR THE PREPARATION OF ARYL ETHERS

PRIORITY OF INVENTION

This application claims priority under 35 U.S.C. §119(e) from U.S. provisional application No. 60/114,092, filed Dec. 29, 1998.

SUMMARY

The present invention relates to an improved method for preparing certain aryl ethers that are useful as antidepressants. The invention also relates to intermediates useful in the method, and to methods for preparing such intermediates.

BACKGROUND OF THE INVENTION

U.S. Pat. No. 4,229,449, issued Oct. 21, 1980, discloses compounds of formula (A)

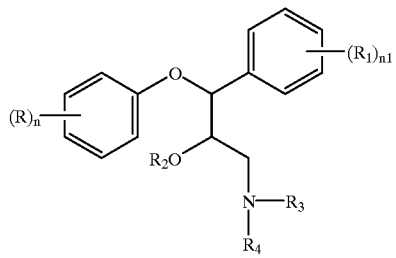

(A)

wherein
  n and n1 are, independently, 1, 2 or 3;
  each of the groups R and $R_1$, which may be the same or different, is hydrogen; halogen; halo-$C_1$–$C_6$alkyl; hydroxy; $C_1$–$C_6$alkoxy; $C_1$–$C_6$alkyl optionally substituted; aryl-$C_1$–$C_6$alkyl optionally substituted; aryl-$C_1$–$C_6$alkoxy optionally substituted; —$NO_2$; $NR_5R_6$ wherein $R_5$ and $R_6$ are, independently, hydrogen or $C_1$–$C_6$ alkyl, or two adjacent R groups or two adjacent $R_1$ groups, taken together, form a —O—$CH_2$—O— radical;
  $R_2$ is hydrogen; $C_1$–$C_{12}$alkyl optionally substituted, or aryl-$C_1$–$C_6$alkyl;
  each of the groups $R_3$ and $R_4$, which may be identical or different, is hydrogen, $C_1$–$C_6$alkyl optionally substituted, $C_2$–$C_4$alkenyl, $C_2$–$C_4$alkynyl, aryl-$C_1$–$C_4$alkyl optionally substituted, $C_3$–$C_7$cycloalkyl optionally substituted, or $R_3$ and $R_4$ with the nitrogen atom to which they are bounded form a pentatomic or hexatomic saturated or unsaturated, optionally substituted, heteromonocyclic radical optionally containing other heteroatoms belonging to the class of O, S and N;
  or $R_2$ and $R_4$, taken together, form a —$CH_2$—$CH_2$— radical;
or a pharmaceutically acceptable salt thereof.

The compounds are disclosed to possess antidepressant activity.

In particular, U.S. Pat. No. 4,229,449 discloses the compound: 2-[α-(2-ethoxyphenoxy)benzyl]morpholine:

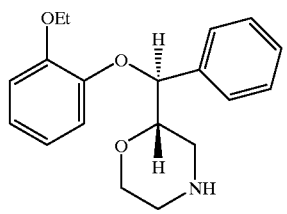

and pharmaceutically acceptable salts thereof, which possess useful antidepressant properties. This compound is also known as Reboxetine.

As illustrated in FIG. 4, U.S. Pat. No. 5,068,433 (issued Nov. 26, 1991) and related U.S. Pat. No. 5,391,735 (issued Feb. 21, 1995) disclose processes and intermediates useful for preparing single diastereomers of compounds of formula VIb:

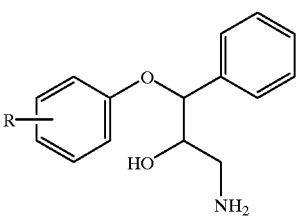

(VIb)

wherein R is $C_1$–$C_6$ alkoxy or tri-halomethyl. These diastereomers are disclosed to be useful intermediates for preparing compounds of formula A, including Reboxetine. The processes disclosed in these patents and in U.S. Pat. No. 4,229,449, however, are inefficient and provide a low overall yield of compounds of formula A when carried out on a commercial scale. Additionally the processes require the use of expensive reagents and require significant production times. Thus, it is not economical to prepare compounds of formula A on a commercial scale using the processes disclosed in these patents.

Accordingly, there is currently a need for improved processes for preparing compounds of formula (A), and for preparing intermediates useful for preparing compounds of formula (A). Ideally, the improved processes should utilize inexpensive reagents, be faster to carry out, or provide improved intermediate or overall yields compared to existing processes. Such improvements would facilitate the commercial scale production of compounds of formula (A).

SUMMARY OF THE INVENTION

As illustrated in FIG. 2, the invention provides a method for preparing an amine of formula VIIa:

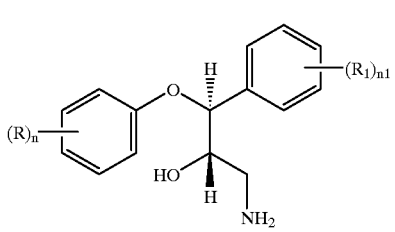

VIIa comprising:
  a) oxidizing an optionally substituted trans-cinnamyl alcohol to give an intermediate epoxide of formula Ia:

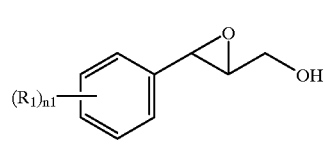

Ia b) reacting the epoxide with an optionally substituted phenol to give a diol of formula IIa:

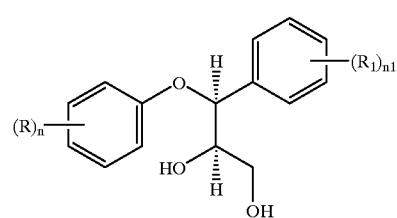

IIa c) reacting the diol with a silylating reagent to give an alcohol of formula IIa:

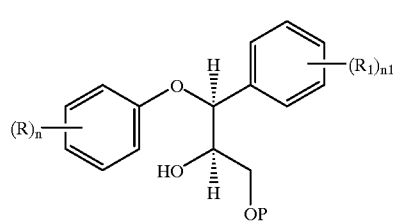

IIIa wherein P is a silyl-linked radical;

d) reacting the alcohol of formula IIIa with reactive derivative of a sulfonic acid to give a compound of formula IVa:

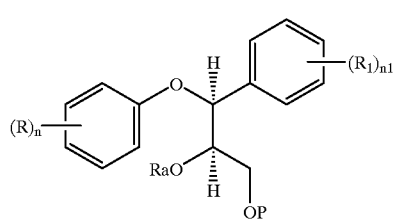

IVa wherein Ra is a residue of a sulfonic acid;

e) removing P from the compound of formula IVa to give an alcohol of formula Va:

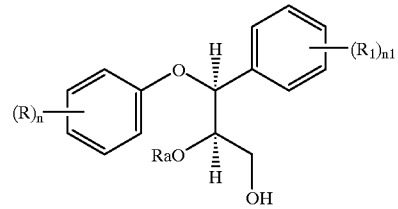

Va f) displacing the sulfonyloxy group to give an epoxide of formula VIa:

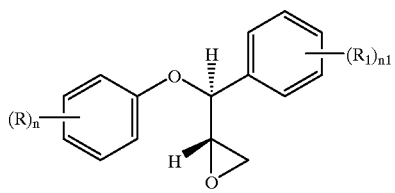

VIa and g) reacting the epoxide with ammonia to give the compound of formula VIIa.

As illustrated in FIG. 3, the invention also provides a method further comprising:

h) reacting a compound of formula VIIa:

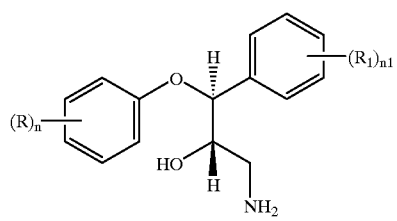

VIIa with a carboxylic acid of formula $HOOCCH_2L$ or a reactive derivative thereof, wherein L is a leaving group, to give an amide of formula VIIIa:

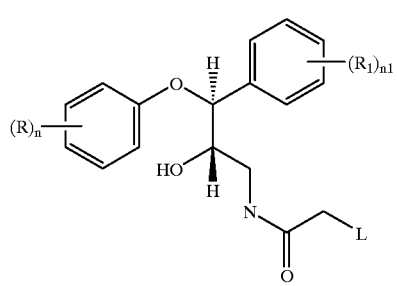

VIIIa i) reacting the compound of formula VIIIa to give a compound of formula IXa:

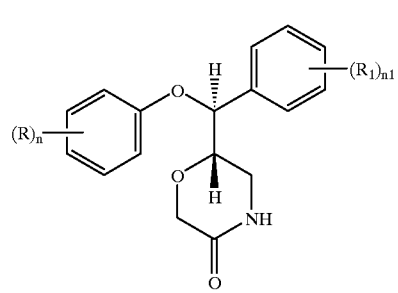

IXa and j) reducing the compound of formula IXa to give a corresponding compound of the following formula:

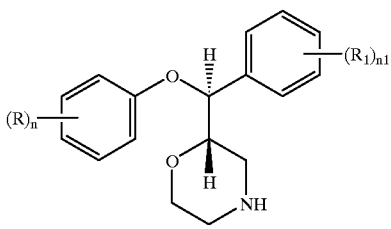

The invention also provides novel intermediates disclosed herein (e.g. compounds of formulae III, IV, V, IIIa, IVa, and Va) as well as methods for their synthesis.

DETAILED DESCRIPTION

Figure 1:
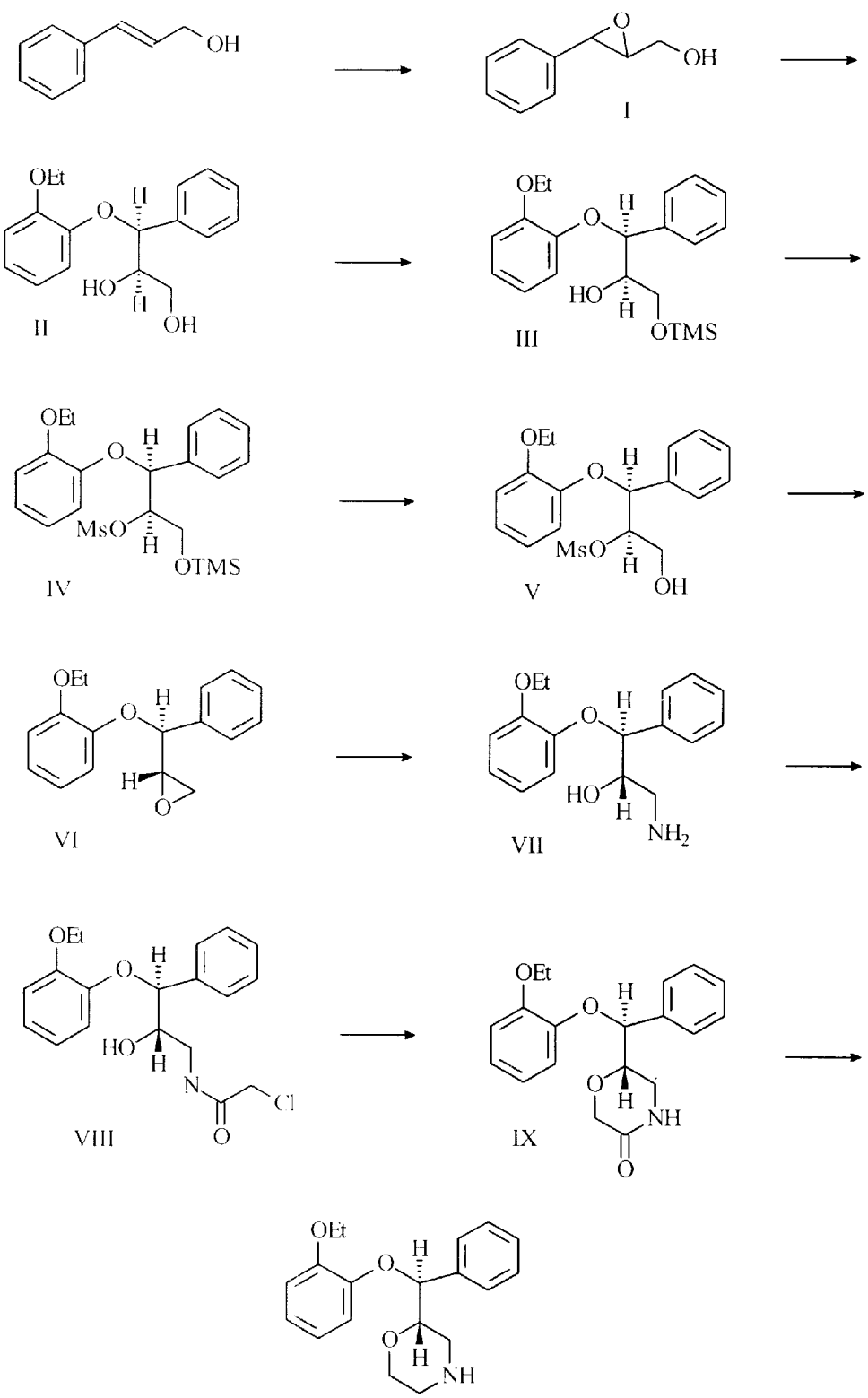
FIG. 1 illustrates a synthetic method of the invention as well as intermediate compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. "Commercial scale" means a multi-kilogram quantity that is sufficient for distribution to a large number of consumers, e.g. at least about 10 kg, about 100 kg, or about 1000 kg of material.

It will be appreciated by those skilled in the art that compounds of formula (A) and the intermediates described herein having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, it being well known in the art how to prepare optically active forms (for example, by resolution of the racemic form by recrystallization techniques, by synthesis from optically-active starting materials, by chiral synthesis, or by chromatographic separation using a chiral stationary phase).

The methods of the invention allow for the preparation of mixtures of single diastereomers of compounds of formula A and the intermediates disclosed herein. It is understood that such mixtures can be separated into the corresponding enantiomers using techniques that are known in the art. Accordingly, the invention also provides for the preparation of single enantiomers of compounds of formula (A) as well as single enantiomers of any of the intermediate compounds disclosed herein. Preferred compounds have stereochemistry that corresponds to the stereochemistry of Reboxetine.

Specific and preferred values listed below for radicals, substituents, and ranges, are for illustration only; they do not exclude other defined values or other values within defined ranges for the radicals and substituents.

Specifically, n is 1.

Specifically, n1 is 1.

Specifically, R is hydrogen, halo, trifluoromethyl, hydroxy, $C_1-C_6$alkoxy, $C_1-C_6$alkyl, aryl-$C_1-C_6$alkyl, aryl-$C_1-C_6$alkoxy, nitro, or $NR_5R_6$.

Specifically, n is 2 and two adjacent R groups form a methylenedioxy radical.

Specifically $R_1$ is hydrogen, halo, trifluoromethyl, hydroxy, $C_1-C_6$alkoxy, $C_1-C_6$alkyl, aryl-$C_1-C_6$alkyl, aryl-$C_1-C_6$alkoxy, nitro, or $NR_5R_6$.

Specifically, n1 is 2 and two adjacent $R_1$ groups form a methylenedioxy radical.

Specifically, $R_5$ and $R_6$ are each hydrogen.

Specifically, $R_2$ is hydrogen, methyl, ethyl, phenyl, benzyl or phenethyl.

Specifically, each of $R_3$ and $R_4$ is hydrogen.

Specifically, at least one $R_3$ and $R_4$ is $C_1-C_6$alkyl optionally substituted, $C_2-C_4$alkenyl, $C_2-C_4$alkynyl, aryl-$C_1-C_4$alkyl optionally substituted, $C_3-C_7$cycloalkyl optionally substituted, or $R_3$ and $R_4$ together with the nitrogen atom to which they are bounded are morpholino, piperidino, N-pyrrolidinyl, N-methyl-piperazinyl or N-phenyl-piperazinyl.

Specifically $R_2$ and $R_4$, taken together form a —$CH_2$—$CH_2$— radical; and $R_3$ is hydrogen.

Specifically, whenever a group can be substituted by "one or more" radicals, the group can be substituted by at least 1, 2, or 3 radicals.

A preferred group of compounds are compounds wherein n is 1 and R is 2-methoxy or 2-ethoxy.

Another preferred group of compounds are compounds wherein n1 is 1 and $R_1$ is hydrogen or halo.

U.S. Pat. Nos. 4,229,449, 5,068,433 and 5,391,735 provide examples of certain specific and preferred values for the substituents and groups described therein. It is to be understood that these specific and preferred values are also specific and preferred values for the corresponding substituents and groups described herein. For example, U.S. Pat. No. 4,229,449 includes the following description for the substituents and groups therein:

a) alkyl, alkenyl, alkynyl and alkoxy groups may be straight or branched chains;

b) when one or more of the groups R and $R_1$ is a substituted $C_1-C_6$ alkyl group, it is preferably $C_1-C_6$ alkyl substituted by one or more substituents chosen from hydroxy, $C_1-C_6$ alkoxy, —$NR_5R_6$, or —C(=O)$NR_5R_6$;

c) aryl is preferably phenyl;

d) when one or more of the groups $R_3$ and $R_4$ is a substituted $C_1-C_6$ alkyl group it is preferably $C_1-C_6$ alkyl substituted by one or more substituents chosen from halogen, hydroxy, $C_1-C_6$ alkoxy, —$NR_5R_6$, or —C(=O)$NR_5R_6$; the same substituents may be present on a substituted $C_1-C_{12}$ alkyl group;

e) substituted aryl-$C_1-C_6$alkyl, aryl-$C_1-C_4$alkyl and aryl-$C_1-C_6$alkoxy groups are preferably aryl-$C_1-C_6$alkyl, aryl-$C_1-C_4$alkyl and aryl-$C_1-C_6$alkoxy groups in which the aryl group is substituted by one or more $C_1-C_6$ alkyl, halogen, halo-$C_1-C_6$alkyl, hydroxy, $C_1-C_6$alkoxy and —$NR_5R_6$;

f) a substituted $C_3-C_7$cycloalkyl group is a $C_3-C_7$cycloalkyl substituted by one or more substituents preferably chosen from $C_1-C_6$alkyl, halogen, halo-$C_1-C_6$-alkyl, hydroxy, $C_1-C_6$alkoxy and —$NR_5R_6$;

g) a $C_1$–$C_6$alkyl group is preferably methyl, ethyl or isopropyl;

h) a $C_1$–$C_{12}$alkyl group is preferably methyl, ethyl, isopropyl or octyl;

i) a $C_2$–$C_4$ alkenyl group is preferably vinyl or allyl; a $C_2$–$C_4$alkynyl group is preferably propargyl;

j) a halo-$C_1$–$C_6$alkyl group is preferably trihalo-$C_1$–$C_6$alkyl, in particular trifluoromethyl;

k) a $C_1$–$C_6$alkoxy group is preferably methoxy or ethoxy;

l) an aryl-$C_1$–$C_6$alkyl or aryl-$C_1$–$C_4$alkyl group is preferably benzyl or phenethyl;

m) an aryl-$C_1$–$C_6$ alkoxy group is preferably benzyloxy;

n) in a —$NR_5R_6$ group, $R_5$ and $R_6$ preferably are, independently, hydrogen or $C_1$–$C_3$ alkyl; in particular methyl, ethyl or isopropyl;

o) a $C_3$–$C_7$cycloalkyl group is preferably cyclopropyl, cyclopentyl or cyclohexyl;

p) when $R_3$ and $R_4$, with the nitrogen atom to which they are linked, form a substituted heteromonocyclic radical, the substituents are preferably $C_1$–$C_6$alkyl or aryl, in particular methyl or phenyl; preferred heteromonocyclic radicals are morpholino, piperidino, N-pyrrolidinyl, N-methyl-piperazinyl and N-phenyl-piperazinyl; and q) when two adjacent R groups or two adjacent $R_1$ groups form the —O—$CH_2$—O— radical, this is preferably a 3,4-methylendioxy radical;

U.S. Pat. No. 4,229,449 also discloses that compounds of formula (A) can be administered as a pharmaceutically acceptable salts, including salts with inorganic acids, for example hydrochloric acid, hydrobromic acid, and sulphuric acid; and including salts with organic acids, for example, citric acid, tartaric acid, methane sulfonic acid, fumaric acid, malic acid, maleic acid and mandelic acid. Preferred salts are disclosed to be acid salts (e.g. the hydrochloric acid or methane sulfonic acid salt) formed with the amine group —$NR_3R_4$. Accordingly, the methods of the invention that yield a compound of formula (A) may also optionally further comprise preparing a salt of the compound of formula (A). Pharmaceutically acceptable salts may be obtained using standard procedures well known in the art.

The epoxidation of an optionally substituted trans-cinnamic alcohol of formula:

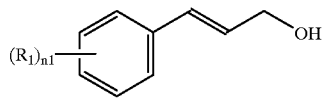

to give an epoxide of formula Ia can conveniently be carried out using a suitable epoxidizing agent, for example, vanadic anhydride and hydrogen peroxide, vanadium (acetylacetonate)$_2$ and tert-butyl hydroperoxide, or a peroxy acid such as perbenzoic acid, m-chloroperbenzoic, peracetic acid, pertrifluoroacetic acid or mono- or di-peroxy-phthalic acid. The reaction can be carried out in any suitable solvent or combination of solvents, for example, in a hydrocarbon, a halogenated hydrocarbon, a linear or branched ether, a carboxylic acid, or an ester. Specific solvents include benzene, toluene, chloroform, methylene chloride, diethyl ether, dioxane, acetic acid, and ethyl acetate. Preferably the reaction is carried out in methylene chloride or ethyl acetate. More preferably in methylene chloride. The reaction can be carried out at any suitable temperature from the freezing point to the reflux temperature of the reaction mixture. Preferably the reaction is carried out at a temperature in the range of about 0° C. to about 50° C. More preferably at a temperature in the range of about 5° C. to about 25° C.

U.S. Pat. No. 5,068,433 and related U.S. Pat. No. 5,391,735 disclose that an epoxide of formula Ib can be prepared from trans-cinnamic alcohol using a suitable oxidizing agent, for instance vanadic anhydride and hydrogen peroxide, or a peroxy acid such as, e.g., perbenzoic acid, m-chloroperbenzoic, peracetic, mono- or di-peroxy-phthalic, or peroxy-trifluoroacetic acid. At Example 1, these patents specifically exemplify the preparation of an epoxide of formula Ib by the oxidation of trans-cinnamic alcohol with m-chloroperbenzoic acid. The oxidation of trans-cinnamic alcohol with m-chloroperbenzoic acid was also reported by P. Melloni et al. *Tetrahedron*, 1985, 41, no. 7, 1393–1399.

m-Chloroperbenzoic acid is expensive to use on a commercial scale. Thus, a different epoxidation reagent would be preferred for the commercial scale production of a compound of formula (A). Studies with mono-peroxy-phthalic acid have shown that this reagent can be used to prepare epoxide Ib on a commercial scale. However, the preparation of mono-peroxy-phthalic acid from phthalic anhydride and hydrogen peroxide is time consuming. Additionally, the epoxidation reaction with mono-peroxy-phthalic acid generates a large amount of solid phthalic acid by-product that must be filtered from the product mixture. This filtration step is time consuming and generates a large amount of aqueous and solid wastes. Thus, m-chloroperbenzoic acid and mono-peroxy-phthalic acid are not ideally suited for the commercial scale epoxidation of trans-cinnamic alcohol.

It has been discovered that the epoxidation of cinnamyl alcohol can conveniently be carried out on a commercially scale using peracetic acid. Peracetic acid is less expensive and, as a liquid, is easier to handle on a large scale than m-chloroperbenzoic acid, which is a solid. Additionally, the use of peracetic acid reduces the time required for preparing epoxide Ib, by eliminating the need to prepare mono-peroxy-phthalic acid; peracetic acid also substantially reduces the amount of aqueous and solid waste generated by the epoxidation reaction compared to the reaction with mono-peroxy-phthalic acid.

Accordingly, the invention provides a method for preparing an epoxide of formula Ia:

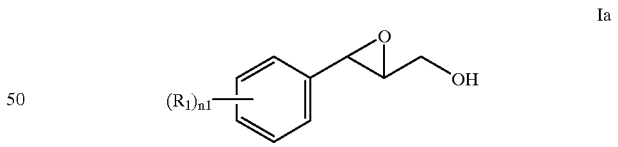

comprising oxidizing a corresponding optionally substituted trans-cinnamic alcohol with peracetic acid. The epoxide Ia is highly sensitive to decomposition by strong acids. Commercial peracetic acid is stabalized with sulfuric acid. Accordingly, the peracetic acid should be treated with a suitable base (e.g. sodium or potassiun acetate) prior to use; or the reaction can conveniently be run in the presence of a suitable solid base (e.g. sodium or potassium carbonate). Preferably, the reaction is carried out on a commercial scale. Preferably, the reaction is carried out in methylene chloride and at a temperature below about 30° C.

The reaction of an epoxide of formula Ia with an optionally substituted phenol to give a diol of formula IIa can conveniently be carried out using a suitable base, for example, aqueous sodium or potassium hydroxide, sodium hydride, or potassium hydride. The reaction can be carried out in any suitable solvent or combination of solvents, for example, in a hydrocarbon, a halogenated hydrocarbon, or a linear or branched ether, such as benzene, toluene, tetrahydrofuran, methylene chloride, diethyl ether, or dioxane. The reaction can be carried out at any suitable temperature from the freezing point to the reflux temperature of the reaction mixture. Preferably the reaction is carried out at a temperature in the range of about 0° C. to about 100° C. More preferably at a temperature in the range of about 20° C. to about 50° C. Preferably, the reaction can be carried out under phase transfer conditions using a suitable phase transfer catalyst (e.g. tributylmethylammonium chloride) as illustrated in Example 2.

P. Melloni et al. *Tetrahedron*, 1985, 41, no. 7, 1393–1399 discloses the isolation of the compound of formula II (FIG. 1) by recrystallization from isopropyl ether. It has been discovered that the compound of formula II can conveniently be isolated by recrystallization from methyl tert-butylether (MTBE). MTBE is less expensive and is less prone to the formation of explosive peroxides than isobutyl ether. Thus, the compound of formula II can preferably be isolated by recrystallization from MTBE.

The protection of the primary hydroxyl group in a diol of formula IIa to form a mono-protected compound of formula IIIa wherein P is a silyl-linked protecting group can be performed using any suitable silylating reagent (e.g. tert-butyldimethylsilyl chloride, trimethylsilyl chloride, tert-butyldiphenylsilyl chloride, triethylsilyl chloride, triisopropylsilyl chloride, hexamethyldisilazane with or without trimethylsilyl chloride, or triphenylsilyl chloride). The reaction can be carried out in any suitable solvent or combination of solvents, for example, in a hydrocarbon, an ester, a halogenated hydrocarbon, or a linear or branched ether, such as benzene, toluene, chloroform, methylene chloride, diethyl ether, tetrahydrofuran, ethyl acetate, or dioxane. The reaction can be carried out at any suitable temperature that allows for the selective protection of the primary alcohol over the secondary alcohol, provided the temperature is above the freezing point of the reaction mixture. Preferably the reaction is carried out at a temperature below −5° C. More preferably, the reaction is carried out at a temperature below −10° C. or below −15° C. Most preferably, the reaction is carried out at a temperature in the range of about −15° C. to about −25° C. Other suitable silylating reagents and reaction conditions are known in the art, for example see Greene, T. W.; Wutz, P. G. M. "Protecting Groups In Organic Synthesis" second edition, 1991, New York, John Wiley & sons, Inc.

Figure 4:
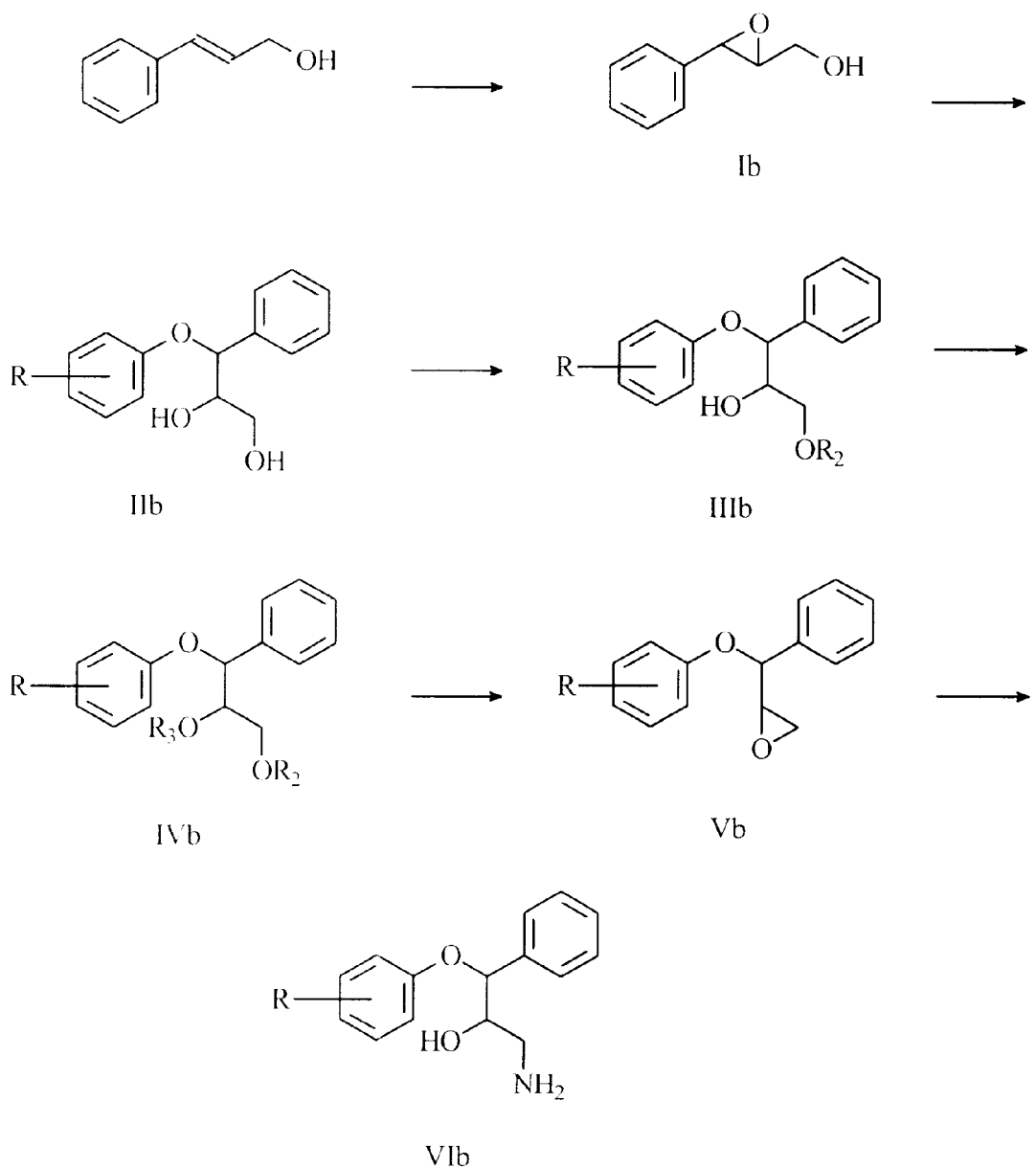
FIG. 4 illustrates the synthesis of a compound of formula VIb.

As illustrated in FIG. 4, U.S. Pat. Nos. 5,068,433 and 5,391,735 disclose that a diol of formula IIb can be esterified to give a compound of formula IIIb wherein $R_2$ is the residue of a carboxylic acid. Unfortunately, protection of the primary alcohol of the diol, under the conditions described in these patents, proceeds with low selectivity; up to 13% of the ester at the secondary alcohol is also formed. Formation of the mono p-nitrobenzoate at the secondary alcohol results in a direct diminution in the yield of the amine of formula VIb. Formation of the mono p-nitrobenzoate at the secondary alcohol also yields the unwanted diastereomer of the amine of formula VIb as a contaminant in the amine product. Additionally, formation of the bis p-nitrobenzoate causes a reduced yield of the amine of formula VIb, and gives the bis p-nitrobenzoate as a contaminant in the product amine. Due to the presence of these unwanted contaminants, there is a need for extensive purification of the amine product, which is time consuming and causes an additional reduction in yield. Thus, the processes described in in U.S. Pat. Nos. 5,068,433 and 5,391,735 are not idealy suited for commercial scale production of the amine of formula VIa.

It has unexpectedly been found that the primary alcohol in the diol of formula IIb can be selectively protected in high yield using a silyl protecting group. In particular, it has been found that the primary alcohol can be selectively protected with a trimethylsilyl group. Reaction with trimethylsilyl chloride is almost completely selective, in both reaction with the primary vs. the secondary alcohol, and in the absence of formation of the bis-trimethylsilyl ether. As a result the yield of amine VIIb obtained from the process of the invention is significantly increased over the yield obtained using the previously known processes. Additionally, trimethylsilyl chloride is less expensive than p-nitrobenzoyl chloride, is more readily available, and is easier to handle on a large scale, since trimethylsilyl chloride is a liquid and p-nitrobenzoyl chloride is a solid.

There is little precedence for the selectivity seen in the reaction of IIb with trimethylsilyl chloride. Trimethylsilyl groups have been used extensively for the derivatization of alcohols, primarily in analytical applications where the intended result is exhaustive silylation. Considerable selectivity has been seen for reactions of secondary alcohols in different environments (for example see H. J. Schneider, R. Horning, *Leibigs Ann. Chem.*, 1974, 1864–1871 and E. W. Yankee et al., *J. Am. Chem. Soc.*, 1974, 5865). However, relative rate information for the reactions of primary and secondary alcohols is unavailable, and the liturature is devoid of examples of the selective protection of a primary alcohol with trimethylsilyl chloride in the presence of a secondary alcohol. Examples for the reaction of a primary alcohol in the presence of a secondary alcohol are reported with hexamathyldisilazane catalyzed by trimethylsilyl chloride (J. Cossy, P. Pale, *Tet. Lett.* 1987, 6039–6040), and by reaction with hexamethyldisilazane catalysed by metal chlorides (H. Firouzabadi, at al., *Syn. Comm.*, 1997, 2709–2719) where the best selectivity was 85:3:12, primary:secondary:bis-ether).

The selective protection of the primary alcohol can be accomplished using a silyl protecting group (preferably trimethylsilyl chloride) at a low temperature. It has also been determined that the migration of the silyl protecting group can be prevented by 1) maintaining the protected compound of formula IIIa at a low temperature throughout the conversion from a compound of formula IIa to a compound of formula Va and 2) by carrying out the required sequence of reactions over a short period of time (e.g. less that about 5 hours, and preferably less than about 4, about 3, or about 2 hours). As illustrated in Example 6, this can conveniently be accomplished by carrying out the conversion of the diol of formula IIa to the compound of formula IIIa, IVa and Va in one reactor, without isolating the intermediates of formula IIIa, IVa.

Accordingly, the invention provides a method to prepare a compound of formula IIIa:

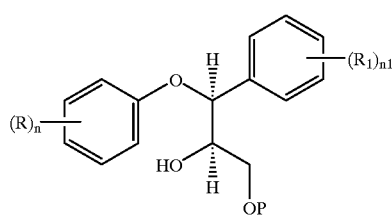

IIIa wherein P is a silyl-linked radical; comprising reacting a diol of formula IIa:

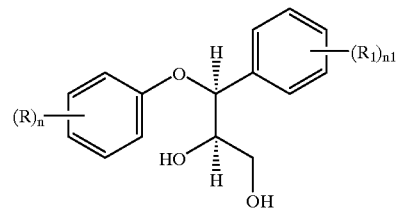

IIa with a suitable silylating reagent. Preferably, P is a trimethylsilyl group, and the silylating reagent is trimethylsilyl chloride. Preferred solvents include ethyl acetate and methylene chloride.

The reaction of an alcohol of formula IIIa with a reactive derivative of a sulfonic acid to give a compound of formula IVa wherein Ra is the residue of a sulfonic acid can be carried out at using any suitable sulfonylating reagent, for example, a sulfonic acid halide, in particular a sulfonic acid chloride (e.g. p-toluenesulfonyl chloride, benzenesulfonyl chloride, ($C_1$–$C_6$)alkylsulfonylchloride, or trifluoromethylsulfonyl chloride). A preferred reactive derivative of a sulfonic acid is methanesulfonyl chloride. The reaction can conveniently be carried out in the presence of a suitable base (e.g. triethyl amine or pyridine). The reaction can be carried out in any suitable solvent or combination of solvents, for example, in a hydrocarbon, a halogenated hydrocarbon, an organic ester, or a linear or branched ether, such as benzene, toluene, tetrahydrofuran, methylene chloride, ethyl acetate, diethyl ether, or dioxane. Preferably, the reaction is carried out in ethyl acetate. The reaction can be carried out at any temperature above the freezing point of the reaction mixture. Preferably the reaction is carried out at a temperature below −5° C. More preferably, the reaction is carried out at a temperature below −10° C. or below −15° C. Most preferably, the reaction is carried out at a temperature in the range of about −15° C. to about −25° C. Other suitable reactive derivative of a sulfonic acid and reaction conditions are known in the art, for example see Jerry March "Advanced Organic Chemistry" fourth addition, 1992, New York, John Wiley & sons, Inc., 352–356.

The removal of the silyl group P from a compound of formula IVa to give an alcohol of formula Va can be carried out using any suitable catalyst, for example, an acid (e.g. HCl) or a fluoride ion source (e.g. tetrabutylammonium fluoride). The reaction can be carried out in any suitable solvent or combination of solvents, for example, in a hydrocarbon, a halogenated hydrocarbon, an organic ester or a linear or branched ether, such as benzene, toluene, chloroform, methylene chloride, ethyl acetate, diethyl ether, tetrahydrofuran, or dioxane. Preferably, the reaction is carried out in ethyl acetate. The reaction can be carried out at any temperature above the freezing point of the reaction mixture. Preferably the reaction is carried out at a temperature in the range from about −78° C. to about 100° C. More preferably, the reaction is carried out at a temperature in the range from about −50° C. to about 50° C. Most preferably, the reaction is carried out at a temperature in the range of about −25° C. to about 25° C.

The reaction of an alcohol of formula Va to give an epoxide of formula VIa can be carried out in the presence of any suitable base, for example, an alkali metal or an alkaline-earth metal hydroxide like sodium or potassium hydroxide. The reaction can be carried out in any suitable solvent or combination of solvents, for example, in a hydrocarbon, a halogenated hydrocarbon, or a linear or branched ether, such as benzene, toluene, chloroform, methylene chloride, diethyl ether, tetrahydrofuran, or dioxane. Preferably, the reaction is carried out under phase transfer conditions in a mixture of toluene and water in the presence of a suitable phase transfer catalyst (e.g. tributylmethyl ammonium chloride). The reaction can be carried out at any temperature above the freezing point and below the reflux temperature of the reaction mixture. Preferably the reaction is carried out at a temperature in the range from about −78° C. to about 100° C. More preferably, the reaction is carried out at a temperature in the range from about −50° C. to about 50° C. Most preferably, the reaction is carried out at a temperature in the range of about 15° C. to about 30° C.

As illustrated in FIG. 4, U.S. Pat. Nos. 5,068,433 and 5,391,735 disclose that a compound of formula IVb can be converted to an epoxide of formula Vb by treatment with a suitable base in an aqueous organic solvent such as, e.g., dioxane or dimethylformamide (see column 4, lines 19–27 and Example 5 therein). P. Melloni et al. *Tetrahedron*, 1985, 41, no. 7, 1393–1399 also disclose the conversion of a specific compound of formula IVb to the corresponding epoxide of formula Vb by treatment with sodium hydroxide in dioxane (see page 1397).

When carried out on a large scale (aproximately 165 kg), this reaction is slow (18 hours), and removal of the dioxane is difficult due to its high boiling point and high freezing point (mp 11.8° C.). Thus, the distillation can require one or two days, and there is a risk the dioxane will freeze in the apparatus during the distillation, causing damage to the condensers. In addition, dioxane is a carcinogen and is toxic.

Figure 2:
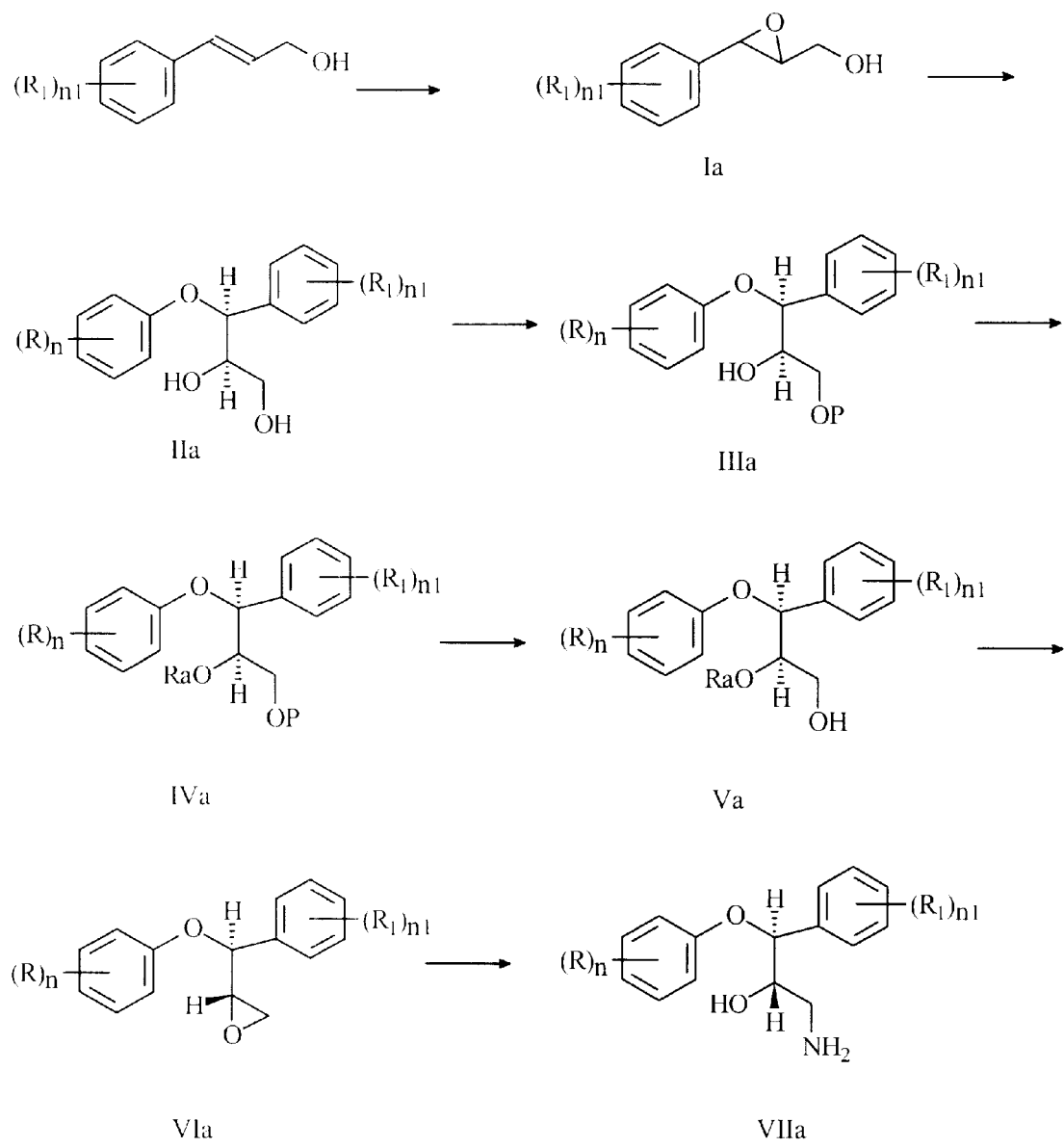
FIG. 2 illustrates a synthetic method of the invention as well as intermediate compounds of the invention.
Figure 3:
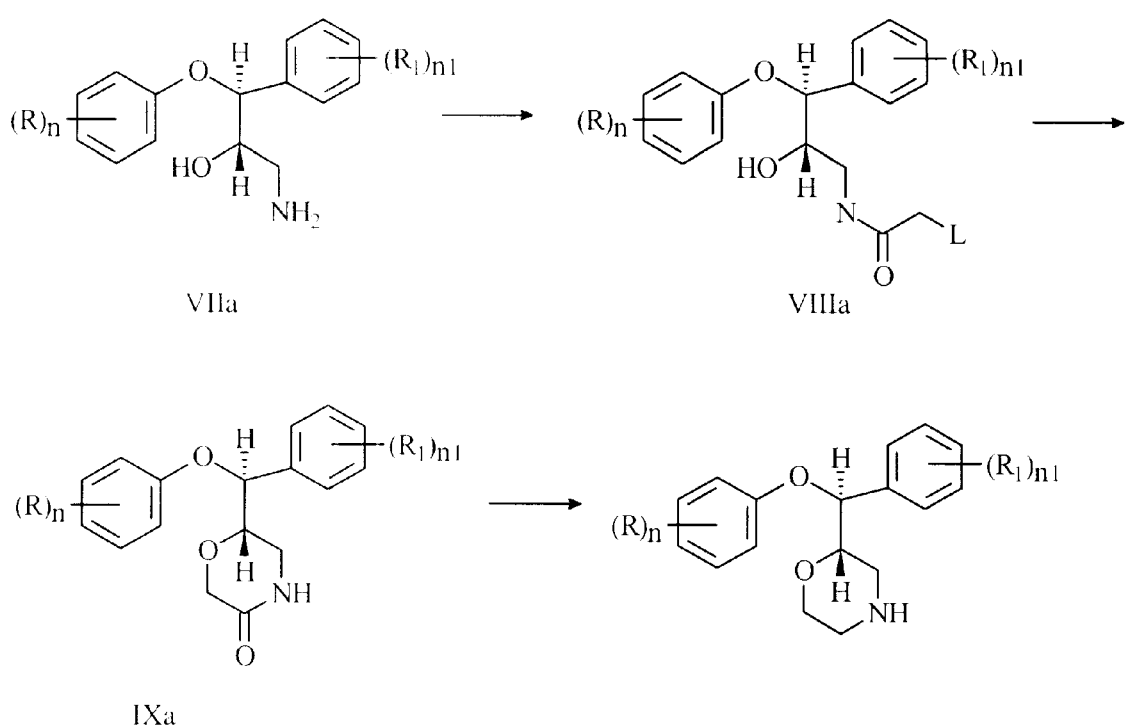
FIG. 3 illustrates a synthetic method of the invention as well as intermediate compounds of the invention.

As illustrated in FIG. 2, and as shown in Example 6 hereinbelow, it has been discovered that a compound of formula Va can be converted to an epoxide of formula VIa in a mixture of toluene and water under phase transfer conditions. The reaction can be carried out on a large scale in about 45 minutes, and the toluene can be readily be removed from the product mixture. Accordingly, the invention provides a method for preparing a compound of formula VIa:

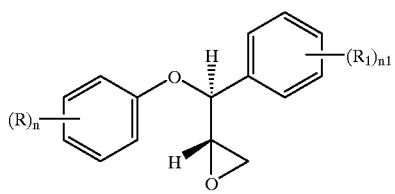

VIa wherein R, $R_1$, n and n1 have any of the values defined herein; comprising treating a corresponding compound of formula Va:

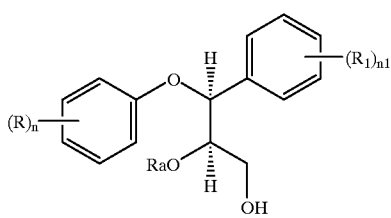
Va wherein Ra is the residue of a sulfonic acid, with a suitable base, under phase transfer conditions. Preferably, the reaction is carried out at a temperature in the range of about 0° C. to about the reflux temperature of the reaction mixture. More preferably, the reaction is carried out at a temperature in the range of about 15° C. to about 35° C.

The reaction of an epoxide of formula VIa with ammonia to give an amine of formula VIIa can be carried out in the presence of any suitable ammonia source, for example, aqueous ammonia or ammonium hydroxide. The reaction can be carried out in any suitable solvent or combination of solvents, for example, a hydrocarbon, a halogenated hydrocarbon, an aliphatic alcohol or a linear or branched ether, such as benzene, toluene, chloroform, methylene chloride, diethyl ether, methanol, ethanol, isopropanol, dioxane, tetrahydrofuran, or dimethylformamide. Preferably, the reaction is carried out in methanol using ammonium hydroxide as an ammonia source, as described in Example 7. The reaction can be carried out at any temperature at or below the reflux temperature of the reaction mixture. Preferably the reaction is carried out at a temperature in the range from about –50° C. to about 100° C. More preferably, the reaction is carried out at a temperature in the range from about 0° C. to about 80° C. Most preferably, the reaction is carried out at a temperature in the range of about 20° C. to about 50° C.

The reaction of an amine of formula VIIa to give a corresponding amide of formula VIIIa can conveniently be carried out with a reactive derivative of a carboxylic acid of formula HOOCCH$_2$L wherein L is a suitable leaving group. Suitable leaving groups are known in the art, and include halides (e.g. bromo, chloro, or iodo), sulfonyl esters (e.g. 4-toluenesulfonyloxy, methylsulfonyloxy, trifluoromethylsulfonyloxy, ($C_1$–$C_6$)alkylsulfonyloxy, or phenylsulfonyloxy, wherein the phenyl may optionally be substituted with one or more substituents independently selected from halo, ($C_1$–$C_6$)alkyl, nitro, ($C_1$–$C_6$)alkoxy, trifluoromethyl, and cyano). A preferred carboxylic acid is chloroacetyl chloride.

The reaction can conveniently be carried out in the presence of a suitable base (e.g. triethylamine or pyridine). The reaction can be carried out in any suitable solvent or combination of solvents, for example, in a hydrocarbon, a halogenated hydrocarbon, an organic ester, or a linear or branched ether, such as benzene, toluene, chloroform, methylene chloride, ethyl acetate, dimethyl carbonate, diethyl ether, tetrahydrofuran, or dioxane. Preferably, the reaction is carried out in dimethyl carbonate or methylene chloride. The reaction can be carried out at any temperature above the freezing point of the reaction mixture. Preferably the reaction is carried out at a temperature below 50° C. More preferably, the reaction is carried out at a temperature below 25° C. or below 15° C. Most preferably, the reaction is carried out at a temperature in the range of about 0° C. to about 10° C.

The reaction of a compound of formula VIIIa to form a morpholinone of formula IXa can conveniently be carried out in the presence of a suitable base (e.g. sodium hydride, potassium hydride, or potassium tert-butoxide). The reaction can be carried out in any suitable solvent or combination of solvents, for example, in a hydrocarbon, a halogenated hydrocarbon, an aliphatic alcohol, or a linear or branched ether, such as benzene, toluene, methylene chloride, diethyl ether, isopropanol, tetrahydrofuran, or dioxane. Preferably, the reaction is carried out in isopropanol with potassium tert-butoxide as a base as described in Example 9. The reaction can be carried out at any temperature above the freezing point and at or below the reflux temperature of the mixture. Preferably the reaction is carried out at a temperature in the range from about –78° C. to about 100° C. More preferably, the reaction is carried out at a temperature in the range from about –25° C. to about 50° C. Most preferably, the reaction is carried out at a temperature in the range of about 0° C. to about 30° C.

The reduction of a morpholinone of formula IXa to form a compound of formula (A) wherein $R_2$ and $R_4$ are ethylene, can conveniently be carried out in the presence of a suitable reducing agent (e.g. borane, lithium aluminum hydride, diisobutylaluminum hydride, diisopropylaluminum hydride, or sodium bis(2-methoxyethoxy)aluminum hydride). The reaction can be carried out in any suitable solvent or combination of solvents, for example, in a hydrocarbon, or in a linear or branched ether, such as benzene, toluene, diethyl ether or tetrahydrofuran. The reaction can be carried out at any temperature above the freezing point and at or below the reflux temperature of the mixture. Preferably the reaction is carried out at a temperature in the range from about –78° C. to about 100° C. More preferably, the reaction is carried out at a temperature below 50° C. or at a temperature below 10° C. Most preferably, the reaction is carried out at a temperature in the range of about –20° C. to about 5° C.

P. Melloni et al. *Tetrahedron*, 1985, 41, no. 7, 1393–1399, at page 1399, disclose that a morpholinone of formula IX (FIG. 1) can be reduced to the corresponding morpholine (Reboxetine) by adding a toluene solution containing 2.96 equivalents of RED-AL (sodium bis(2-methoxyethoxy) aluminum hydride) to a solution of the morpholinone. When this reaction is carried out on a large scale (approximately 25 kg of morpholinone), the reaction product is typically contaminated with 0.6 to 1% of the following impurity:

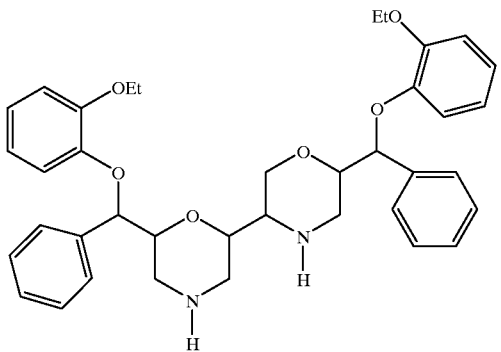

For the final drug product of formula (A) to comply with regulatory requirements in some countries, the concentration of this inpurity in the final product must be less than 0.1%. Removal of this impurity is difficult, but can be accomplished using a controlled pH extraction at about pH 5.2. During this extraction, however, 20–30% of the compound of formula (A) is typically lost and cannot be readily recovered.

It has been determined that the quantity of impurity that results from the reduction can be significantly reduced by adding a solution of the morpholinone IXa to a solution containing an excess (e.g. about 5 equivalents) of the sodium bis(2-methoxyethoxy)aluminum hydride. Using this procedure, the reaction has been found to directly yield Reboxetine free base containing less than 0.1% of the impurity. This material can be used directly, without carrying out a controlled pH extraction. This reduces processing time and eliminates the loss of 20–30% of the product.

Use of less than 5 equivalents of the reducing agent was found to reduce the yield for the reaction. Thus, the reduction is preferably carried out using at least about 4 equivalents of sodium bis(2-methoxyethoxy)aluminum hydride, or another suitable reducing agent. More preferably, the reduction is carried out using at least about 5 equivalents of a suitable reducing agent (e.g. at least about 5 to about 10 equivalents of sodium bis(2-methoxyethoxy)aluminum hydride). Preferably, the reducing agent is not lithium aluminum hydride.

Accordingly, the invention provides a method for preparing a compound of the following formula:

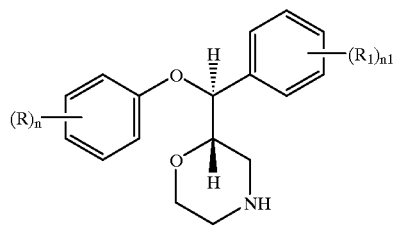

wherein R, $R_1$, n and n1 have any of the values defined herein; comprising adding a corresponding compound of formula XIa:

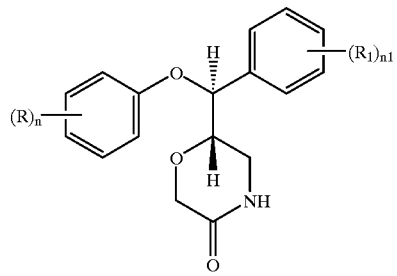

to a solution comprising at least 4 equivalents of a suitable reducing agent.

The invention also provides a compound of formula formula IIIa:

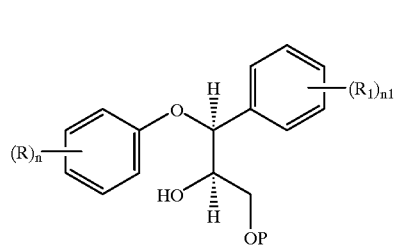

wherein R, $R_1$, n, and n1 have any of the values, specific values or preferred values described herein for a corresponding radical in a compound of formula (A), and P is a suitable silyl protecting group (e.g. tert-butyldimethylsilyl, trimethylsilyl, tert-butyldiphenylsilyl, triethylsilyl, triisopropylsilyl, triphenylsilyl). Preferably, the compound of formula IIIa is a compound of formula III.

The invention also provides a compound of formula IVa:

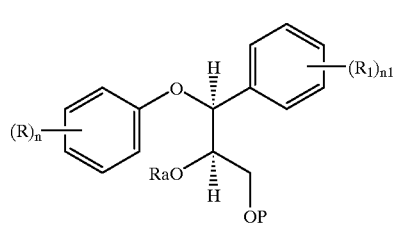

wherein R, $R_1$, n, and n1 have any of the values, specific values or preferred values described herein above for a corresponding radical in a compound of formula (A); P is a suitable silyl protecting group (e.g. tert-butyldimethylsilyl, trimethylsilyl, tert-butyldiphenylsilyl, triethylsilyl, triisopropylsilyl, triphenylsilyl); and Ra is a residue of a sulfonic acid (e.g. p-toluenesulfonyl, phenylsulfonyl, methylsulfonyl, ethylsulfonyl, or trifluoromethylsulfonyl. Preferably, the compound of formula IVA is a compound of formula IV.

The invention also provides a compound formula Va:

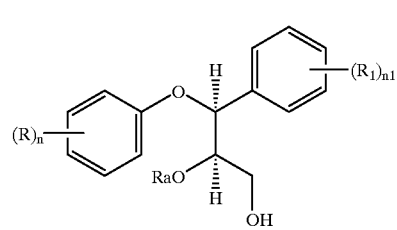

wherein R, $R_1$, n, and n1 have any of the values, specific values or preferred values described herein above for a corresponding radical in a compound of formula (A); and Ra is a residue of a sulfonic acid (e.g. p-toluenesulfonyl, phenylsulfonyl, methylsulfonyl, ethylsulfonyl, or trifluoromethylsulfonyl. Preferably, the compound of formula Va is a compound of formula V.

As illustrated in FIG. 1, the invention also preferably provides a method to prepare a compound of formula VII:

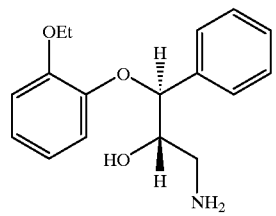

comprising:

a) oxidizing an optionally substituted trans-cinnamyl alcohol to give an intermediate epoxide of formula I:

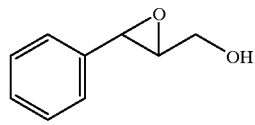
I b) reacting the epoxide with an optionally substituted phenol to give a diol of formula II:

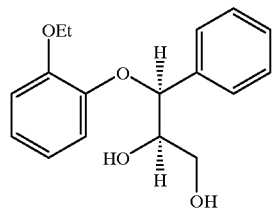
II c) reacting the diol with a silylating reagent to give an alcohol of formula III:

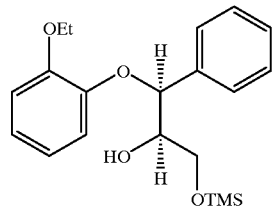
III d) reacting the alcohol of formula III with reactive derivative of methane sulfonic acid to give a compound of formula IV:

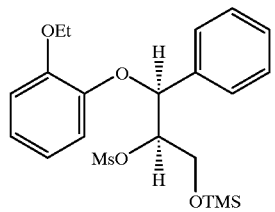
IV e) removing the trimethylsilyl group from the compound of formula IV to give an alcohol of formula V:

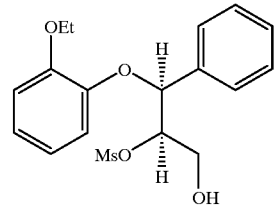
V f) displacing the sulfonyloxy group to give an epoxide of formula VI:

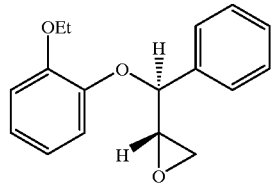
VI and g) reacting the epoxide with ammonia to give the compound of formula VII.

The resulting compound of formula VII can conveniently be isolated by conversion to the methane sulfonate salt, for example, as described in Example 7.

The above method for preparing a compound of formula VII can optionally further comprise:

h) reacting the compound of formula VII with chloroacetyl chloride to give an amide of formula VIII:

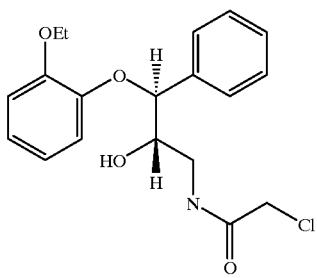
VIII i) reacting the compound of formula VIII to give a compound of formula IX:

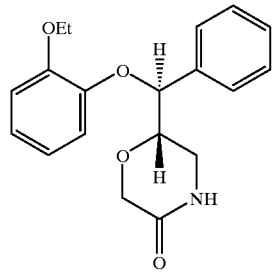
IX and j) reducing the compound of formula IX to give a corresponding morpholine compound of the following formula:

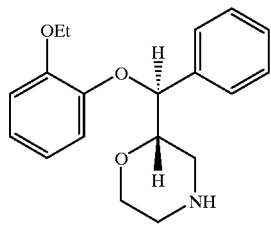

The invention will now be illustrated by the following non-limiting Examples wherein unless otherwise stated:

a) melting points were determined in open capillary tubes in a Buchi melting point apparatus and are uncorrected;

b) NMR spectral data were recorded on a Bruker AMX400 operating at 400.13 MHz for the observation of $^1$H and at 100.62 for the observation of $^{13}$C; samples were dissolved in and internally referenced to CDCl$_3$ ($^1$H δ=7.26; $^{13}$C, δ=77.0);

c) mass spectral data were aquired on a Fisons Trio 2000 single quodrupole spectrometer operating in electron impact (EI) or chemical ionization (CI) mode; the scan range was 110–600 amu for CI and 45–600 amu for EI; source temperature was 150° C., electron multiplier 400 V, and electron energy −70 eV; chemical ionization was performed with ammonia as reagent gas and adjusted to a source pressure of $1.4\times10^{-4}$ mTorr;

d) reactions were routinely monitored using a Perkin Elmer HPLC (Series 200 pump and 235C diode array detector) using Nucleosil-100 C-18 columns and mixtures of water and acetonitrile as the eluent, with or without added CF$_3$COOH; conversion of cinnamyl alcohols to epoxides were monitored at 215 nm, all others at 275 nm;

e) reagents and solvents were commercial products and were used without purification;

f) reactions were run under nitrogen; and g) thin layer chromatography (TLC) was performed using Analtech uniplate silica gel plates (250μ, Cat. no. 02521).

EXAMPLES

Example 1

(2RS,3RS)-2,3-Epoxy-3-phenylpropanol (I)

Sodium carbonate (224 g) and trans-cinnamyl alcohol (200.0 g) were mixed with 2 L of methylene chloride, a slow nitrogen sweep was maintained through the vapor space of the flask and the mixture was cooled to 15–20° C. with a cold water bath. Peracetic acid solution (35%, 381.2 mL) was added over a 3 hour period, maintaining the internal temperature below 25° C. After the peracetic acid addition was complete, the mixture was stirred for 2–3 hours until complete, as shown by HPLC analysis. The mixture was cooled to 10° C. with an ice bath, and a solution of sodium sulfite (160 g) in 1200 ml water was added slowly over 90 minutes, keeping the temperature below 30° C. The phases were separated and the aqueous phase was extracted with methylene chloride (200 mL) to give a solution of the title compound.

Example 2

(2RS,3SR)-3-(2-Ethoxyphenoxy)-2-hydroxy-3-phenylpropanol (II)

Water (800 mL), sodium hydroxide (50%, 83.1 mL), tributylmethyl-ammonium chloride (75%, 27.5 ml), and 2-ethoxyphenol (306.72 g) were combined and stirred at 20–25° C. The methylene chloride solution of 2,3-epoxy-3-phenylpropanol from Example 1 was added, and the two phase mixture was stirred and heated to 40° C. internal temperature. The methylene chloride was distilled at atmospheric pressure over a 3–4 hour period. When the methylene chloride had been removed, the internal temperature was raised to 60° C. for 2 hours. The mixture was cooled to below 30° C., toluene (1200 ml) was added, and the mixture was stirred for 5 minutes. The phases were separated and the aqueous phase was extracted with toluene (800 mL). The toluene solutions were combined and washed with 1 N NaOH (2×400 ml) and with water (400 mL) at approximately 25° C. The toluene solution was concentrated under partial vacuum maintaining an internal temperature of 40–50° C. The residual oil was dissolved in methyl t-butyl ether (760 ml), and water content was verified to be less than 0.1% by potassium fluoride assay. The solution was seeded with crystals of the title compound at 20–25° C., stirred for 1 hour, and cooled to 0° C. for 2 hours. The resulting solids were filtered, washed with methyl t-butylether (2×200 mL, cooled to −15° C.), and dried under vacuum to yield 256.1 g of the title compound (60.5% from cinnamyl alcohol).

Example 3

(2RS,3SR)-3-(2-Ethoxyphenoxy)-2-hydroxy-3-phenyl-1-(trimethylsilyloxy)propane (III)

3-(2-Ethoxyphenoxy)-2-hydroxy-3-phenylpropanol from Example 2 (1.44 g, 5 mmole) and triethylamine ((0.77 mL, 5.5 mmole) were dissolved in ethyl acetate (15 ml) and cooled to −17° C. Trimethylsilyl chloride (0.64 mL, 5.0 mmole) dissolved in 5 mL of ethyl acetate was added over 10 minutes keeping the temperature below −15° C. a white precipitate formed during this addition. The mixture was stirred below −15° C. for 15 minutes, and 20 mL of pentane was added. The solids were removed by filtration and the filtrate was concentrated under vacuum to a cloudy oil. The oil was chromatographed on silica (230–400 mesh) eluting with 4:1 heptane-ethyl acetate. The product-containing fractions were concentrated to yield 1.80 g (88.5%) of the title compound as a clear colorless oil; $^1$H NMR (400.13 MHZ, CDCl$_3$) d 0.09 (s, 9H), 1.47 (t, J=6.8 Hz, 3H), 2.82 (d, J=5.2, 1H), 3.80 (m, 3H), 4.0–4.11 (m, 4H), 5.08 (d, J=6.0, 1H), 6.76 (m, 2H), 6.85 (m, 2H), 7.2–7.45 (m, 5H); $^{13}$C NMR (100.62 MHZ, CDCl$_3$) d 0.0, 15.54, 63.34, 65.06, 75.22, 83.71, 114.28, 118.60, 121.51, 122.95, 127.84, 128.49, 128.84, 138.93, 148.34, 150.40; MS (ei) m/e 360.

Example 4

(2RS,3SR)-3-(2-Ethoxyphenoxy)-2-mesyloxy-3-phenyl-1-(trimethylsilyloxy)propane (IV)

3-(2-Ethoxyphenoxy)-2-hydroxy-3-phenylpropanol from Example 2 (1.44 g, 5 mmole) and triethylamine ((0.77 mL, 5.5 mmole) were dissolved in ethyl acetate (15 mL) and cooled to −17° C. Trimethylsilyl chloride (0.64 mL, 5.0 mmole) dissolved in ethyl acetate (5 mL) was added over 10 minutes keeping the temperature below −15° C. A white precipitate formed during this addition. The mixture was stirred below −15° C. for 15 minutes. Triethylamine (0.8 mL, 5.7 mmole) was added, followed by methanesulfonyl chloride (0.46 mL, 6.0 mmole) dissolved in 5 mL of ethyl acetate, keeping the temperature below −15° C. The mixture was stirred below −15° C. for 15 minutes. Pentane (20 mL) was added and the solids were removed by filtration. The filtrate was concentrated under vacuum to a cloudy oil. The oil was chromatographed on silica (230–400 mesh) eluting with 4:1 heptane-ethyl acetate. The product-containing fractions were concentrated to yield 2.00 g (91.2%) of the title compound as an oil that solidified on standing; mp 80–82.5° C.; $^1$H NMR (400.13 MHZ, CDCl$_3$) d 0.17 (s, 9H), 1.50 (t, J=6.8 Hz, 3H), 3.06 (s, 3H), 3.77 (dd, J=11, 6, 1H), 4.00 (dd, J=11, 6, 1H), 4.10, (q, J=6.8, 2H), 5.07, (m, 1H), 5.51 (d, J=4.4, 1H), 6.75 (m, 2H), 6.91 (m 2H), 7.2–7.49 (m, 5H); $^{13}$C NMR (100.62 MHZ, CDCl$_3$) d 0.0, 15.66, 38.87, 61.57, 64.88, 79.90, 85.20, 113.97, 116.99, 121.32, 122.79, 128.26, 129.09, 129.14, 136.75, 147.72, 149.95; MS (ei) m/e 438.

Example 5

(2RS,3SR)-3-(2-Ethoxyphenoxy)-2-mesyloxy-3-phenyl-1-propanol (V)

3-(2-Ethoxyphenoxy)-2-hydroxy-3-phenylpropanol from Example 2 (0.288 g, 1 mmole) and triethylamine ((0.15 mL, 1.1 mmole) were dissolved in ethyl acetate (5 mL) and cooled to −17° C. Trimethylsilyl chloride (0.13 mL, 1.0 mmole) dissolved in ethyl acetate (2 mL) was added over 10 minutes keeping the temperature below −15° C. a white precipitate formed during this addition. The mixture was stirred below −15° C. for 15 minutes. Triethylamine (0.15 mL, 1.1 mmole) was added, followed by methanesulfonyl chloride (0.085 mL, 1.1 mmole) dissolved ethyl acetate (2 mL) keeping the temperature below −15° C. The mixture was stirred below −15° C. for 15 minutes. Hydrochloric acid (2N, 2 mL) was added and the mixture was allowed to warm to 20–25° C. and stirred for 30 minutes. The phases were separated and the organic phase was washed with saturated aqueous sodium chloride solution (5 mL) and dried over sodium sulfate. The solution was evaporated to yield 0.377 g of an oil. The oil was chromatographed on silica (230–400 mesh) eluting with 1:1 hexane-ethyl acetate. The product-containing fractions were concentrated to yield 0.33 g (91%) of the title compound as an oil that solidified on standing; mp 83–86° C.; $^1$H NMR (400.13 MHZ, CDCl$_3$) d 1.66 (t, J=8.2 Hz, 3H), 2.85 (s, 3H), 4.14–4.35 (m, 4H), 5,12 (m, 1H), 5.52 (d, J=6.1 Hz), 6.8–7.15 (m, 4H), 7.5–7.7 (m, 5H); $^{13}$C NMR (100.62 MHZ, CDCl$_3$) d 14.73, 37.80, 62.19, 64.27, 81.40, 84.04, 112.88, 117.19, 120.67, 122.86, 127.40, 128.77, 128.86, 137.02, 146.40, 149.30; MS (ei ) m/e 366.

Example 6

(2RS,3RS)-1,2-Epoxy-3-(2-ethoxyphenoxy)-3-phenylpropane (VI)

3-(2-Ethoxyphenoxy)-2-hydroxy-3-phenyl-1-propanol from Example 2 (28.8 g) and triethylamine (16.7 mL) were dissolved in ethyl acetate (170 ml) and cooled to −20 to −15° C. a solution of trimethylsilyl chloride (13.2 ml) in ethyl acetate (20 ml) was added keeping the reaction temperature between −20 and −15° C. After the addition was complete, the mixture was stirred for 5 minutes at −20 to −15° C.

Methanesulfonyl chloride (9.3 ml) was added to the solution keeping the temperature between −20 and −15° C. Triethylamine (16.7 ml) was then added, again maintaining a temperature between −20 and −15° C. The mixture was stirred for 15 minutes after completion of triethylamine addition.

A solution of concentrated hydrochloric acid (8.3 ml) and water (92 ml) was added to the reaction mixture. The mixture was allowed to warm to 15–25° C. and stirred for 45 minutes. The reaction was monitored by TLC. The phases were separated and the organic phase was washed with a solution of sodium bicarbonate (5 g) in 45 ml of water and then with a solution of 12.5 grams sodium chloride and 37.5 ml of water. The organic phase was concentrated under vacuum to an oil. Toluene (200 ml) was added and the solution was concentrated to an oil, which was redissolved in 200 ml of toluene.

Sodium Hydroxide solution (50%, 36 g) water (60 mL), and tributylmethylammonium chloride (70%, 2.5 g) was added to the toluene solution. The mixture was purged with nitrogen, stirred at a high rate at 20–25° C. for 45 minutes, and analyzed by HPLC. The phases were separated and the oily yellow interface was kept with the organic phase. The aqueous phase was extracted with toluene (50 mL) and the toluene solutions were combined. The toluene solutions were washed with saturated sodium chloride solution (50 mL, 12.5 grams of NaCl and 37.5 ml of water). The toluene solution was concentrated under vacuum to 60 ml (bath temperature 40° C.). Methanol (300 ml) was added and the solution was concentrated to a volume of 60 ml. Methanol (300 ml) was added and the mixture was again concentrated to a volume of 60 ml to give a solution of the title compound.

Example 7

(2RS,3RS)-3-(2-Ethoxyphenoxy)-2-hydroxy-3-phenylpropylamine (VII)

To the methanol solution from Example 6 was added 270 ml of methanol and 300 ml of ammonium hydroxide. The mixture was stirred in a sealed vessel and heated to 40° C. for three hours. After three hours the reaction was cooled and analyzed by HPLC. Methylene chloride (223 ml) was added and the mixture was stirred and then allowed to settle. The phases were separated and the aqueous phase was extracted with methylene chloride (2×100 ml). The organic layers were combined and distilled under vacuum to a volume of 300 ml. Methylene chloride (180 ml) was added back to the solution. The methylene chloride solution was washed with 250 ml of water. The water was extracted with 100 ml of methylene chloride and the methylene chloride solutions were combined.

A solution of 250 ml of water and 10 ml of concentrated hydrochloric acid was added to the combined methylene chloride solutions. The pH was adjusted to below 2 by the addition of more HCl. The mixture was stirred and then allowed to settle. The phases were separated and the organic phase was extracted with 250 ml of water. The aqueous phases were combined and washed with 46 ml of methylene chloride.

Methylene chloride (144 ml) was added to the aqueous phase and the pH was adjusted to greater than 12 with 50% aqueous NaOH (approximately 10 gr). The phases were separated and the aqueous phase was extracted with 72 ml of methylene chloride. The organic phases were combined and distilled to a volume of 200 ml. Isopropyl alcohol (200 ml) was added and the mixture distilled to a volume of 200 ml. Isopropyl alcohol (200 ml) was added and the solution again distilled to a volume of 200 ml. Methanesulfonic acid (7.9 g) was added and the mixture was stirred at 20–25° C. for 2 hours. The resulting slurry was cooled to 0–5° C. and stirred for 60 minutes. The solids were filtered and washed with 100 ml of isopropyl alcohol. The resulting solid was dried in a vacuum oven at 60° C. to yield 24.5 g of the title compound as the methane sulfonate salt (64% overall from 3-(2-ethoxyphenoxy)-2-hydroxy-3-phenyl-1-propanol).

Example 8

(2RS,3SR)-N-Chloroacetyl-3-(2-ethoxyphenoxy)-2-hydroxy-3-phenylpropylamine (VIII)

(2RS,3RS)-1,2-Epoxy-3-(2-ethoxyphenoxy)-3-phenylpropane (47.7 g) and dimethyl carbonate (700 mL)

were stirred to form a white slurry. Triethylamine (52 mL) was added and the mixture cooled to 6–10° C. using an ice/$H_2O$ bath, a solution of chloroacetyl chloride (13.8 mL) in dimethyl carbonate (50 mL) was added over a 30 minute period keeping the temperature between 4–10° C. The mixture was stirred for 1 hour. The mixture was washed with 500 mL of $H_2O$ and then with 500 mL of 3% aqueous NaCl solution. The organic layer was concentrated under vacuum at 40° C. to yield a dark oil. Isopropanol (500 mL) was added and the mixture again concentrated to remove any residual dimethyl carbonate, yielding the title compound.

Example 9

(2RS,3RS)-2-[α-(2-Ethoxyphenoxy)benzyl]morpholine-5-one (IX)

The product from Example 8 was stirred with 200 mL of isopropanol to form a slurry. A solution of isopropanol (305 mL) and potassium t-butoxide (30.6 g) was prepared. This was added to the isopropanol slurry maintaining the temperature of the reaction between 20–23° C. with an ice bath. The mixture was stirred at 20–25° C. for 1 hour. The pH of the mixture was adjusted to 6.4 by the addition of 1N HCl (approx 210 mL). The mixture was evaporated under vacuum to an oil. Water (170 mL) toluene (150 mL) were added to the residue and the mixture was stirred for 5 minutes. The aqueous layer was extracted with 100 mL of toluene. The toluene extracts were combined and washed with 100 mL of 1N HCl and 100 mL of 10% NaCl solution. The toluene solution was evaporated to an oil and the residue was redissolved in 240 mL of toluene to give a solution of the title compound.

Example 10

(2RS,3RS)-2-[α-(2-Ethoxyphenoxy)benzyl]morpholine (Reboxetine)

Vitride solution in toluene (65%, 187 mL) was diluted with 187 mL of toluene and the solution cooled to below 5° C. The toluene solution from Example 9 was added over 1 hour maintaining the temperature below 5° C. The mixture was stirred for 15 minutes after completion of the addition. A solution of 60 g of 50% NaOH in sufficient water to make a volume of 350 mL was added, keeping the temperature below 55° C. The two phase mixture was stirred at 55° C. for 15 minutes after completion of the addition. The toluene phase was washed with 5% sodium carbonate solution (3×170 mL). Water was added to the toluene solution and 1N HCl was added to give a pH of 3.11. The aqueous phase was extracted with 480 mL of toluene. Toluene (480 mL) was added to the aqueous solution and the pH wad adjusted to above 12 with 50% NaOH. The aqueous phase was extracted with 240 mL of toluene. The two toluene solutions were combined and washed with sodium carbonate solution (5%, 175 mL) and water (175 mL). The toluene was evaporated to yield 32 g of the title compound as the free base.

Example 11

(2RS,3RS)-2-[α-(2-Ethoxyphenoxy)benzyl]morpholine methanesulfonate salt

The oil from Example 10 was dissolved in 122 mL of acetone and stirred with 2 g of activated carbon (for example, Darco G-60, Calgon Carbon Corporation; or Norit, American Norit Corporation) and 2 g of celite at 20–25° C. for 1 hour. The mixture was filtered and the volume of the filtrate was adjusted to 320 mL. The solution was cooled to 0° C. and methanesulfonic acid (5.1 mL) was added. The mixture was stirred at 0° C. for 70 minutes, then filtered. The solids were washed with 100 mL of acetone and dried under nitrogen to yield 30.08 g of white solids. The solids were slurried in 200 mL of acetone and stirred at 50° C. for 2 hours. The slurry was cooled to 0° C. for 30 minutes and filtered. The solids were dried under nitrogen to yield 27.72 g of the title compound (54.3% overall from 3-(2-ethoxyphenoxy)-2-hydroxy-3-phenylpropylamine).

All publications, patents, and patent documents referenced herein, as well as the entire disclosure of U.S. provisional application No. 60/114,092, are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing an amine of formula VIIa:

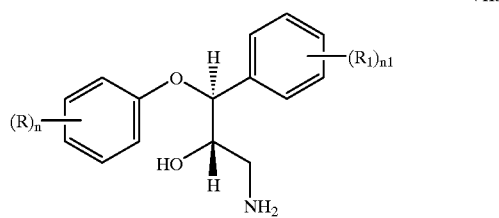

VIIa wherein n and n1 are, independently, 1, 2 or 3; and each or the groups R and $R_1$, which may be the same or different, is hydrogen; halogen; halo-$C_1$–$C_6$alkyl; hydroxy; $C_1$–$C_6$alkoxy; $C_1$–$C_6$alkyl optionally substituted; aryl-$C_1$–$C_6$alkyl optionally substituted; aryl-$C_1$–$C_6$alkoxy optionally substituted; —$NO_2$; $NR_5R_6$ wherein $R_5$ and $R_6$ are, independently, hydrogen or $C_1$–$C_6$ alkyl, or two adjacent R groups or two adjacent $R_1$ groups, taken together, form a —O—CH2-O— radical; comprising:

a) oxidizing an optionally substituted trans-cinnamyl alcohol to give an intermediate epoxide of formula Ia:

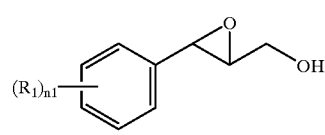

Ia b) reacting the epoxide with an optionally substituted phenol to give a diol of formula IIa:

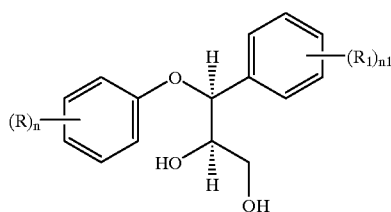

c) reacting the diol with a silylating reagent to give an alcohol of formula IIIa:

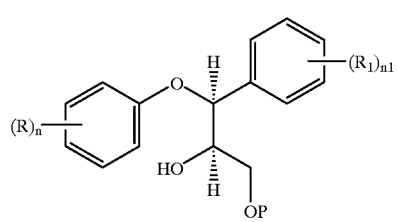

wherein P is a silyl-linked radical;

d) reacting the alcohol of formula IIIa with reactive derivative of a sulfonic acid to give a compound of formula IVa:

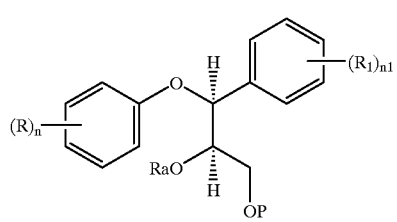

wherein Ra is a residue of a sulfonic acid;

e) removing P from the compound of formula IVa to give an alcohol of formula Va:

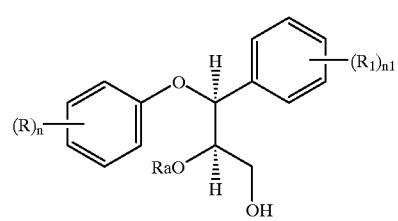

f) displacing the sulfonyloxy group to give an epoxide of formula VIa:

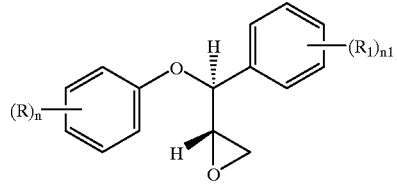

and g) reacting the epoxide with ammonia to give the compound of formula VIIa.

2. The method of claim 1 further comprising:

h) reacting a compound of formula VIIa:

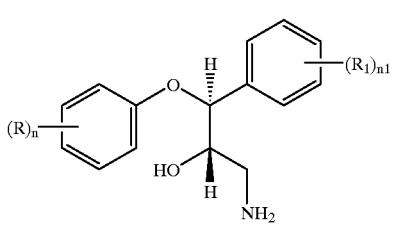

with a carboxylic acid of formula $HOOCCH_2L$ or a reactive derivative thereof, wherein L is a suitable leaving group, to give an amide of formula VIIIa:

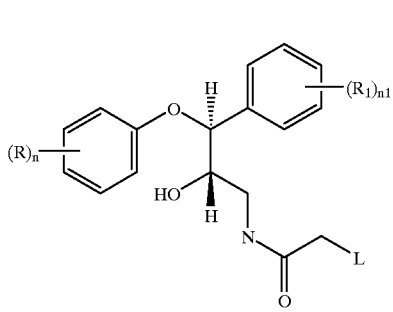

i) reacting the compound of formula VIIIa to give a compound of formula IXa:

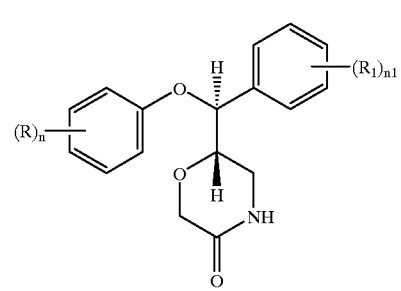

and j) reducing the compound of formula IXa to give a corresponding morpholine compound of the following formula:

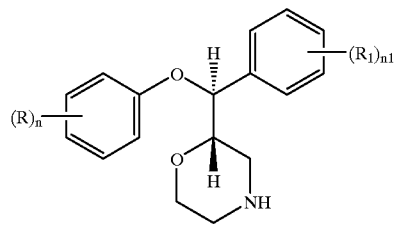

3. The method of claim 2 further comprising forming a pharmaceutically acceptable salt of the morpholine compound.

4. A method to prepare a compound of formula VII:

VII

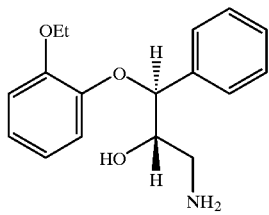

comprising:

a) oxidizing an optionally substituted trans-cinnamyl alcohol to give an intermediate epoxide of formula I:

I

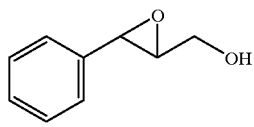

b) reacting the epoxide with an optionally substituted phenol to give a diol of formula II:

II

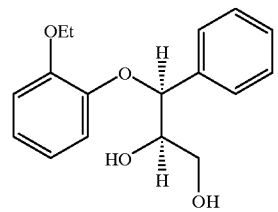

c) reacting the diol with a silylating reagent to give an alcohol of formula III:

III

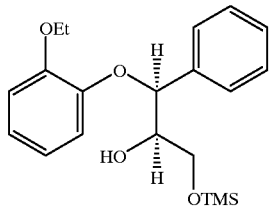

d) reacting the alcohol of formula III with reactive derivative of methylsulfonic acid to give a compound of formula IV:

IV

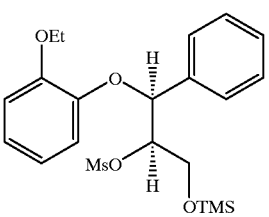

e) removing the trimethylsilyl group from the compound of formula IV to give an alcohol of formula V:

V

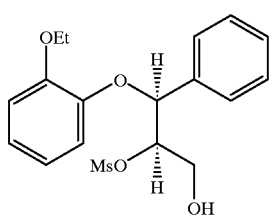

f) displacing the sulfonyloxy group to give an epoxide of formula VI:

VI

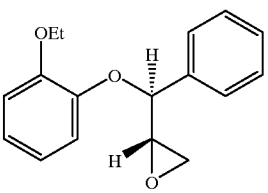

and g) reacting the epoxide with ammonia to give the compound of formula VII.

5. The method of claim 4 further comprising preparing the methane sulfonate salt of the compound of formula VII.

6. The method of claim 4 further comprising:

h) reacting the compound of formula VII with chloroacetyl chloride to give an amide of formula VII:

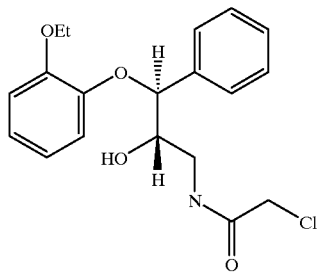

VIII i) reacting the compound of formula VIII to give a compound of formula IX:

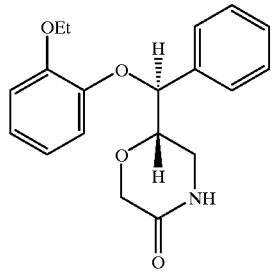

IX and j) reducing the compound of formula IX to give a corresponding morpholine compound of the following formula:

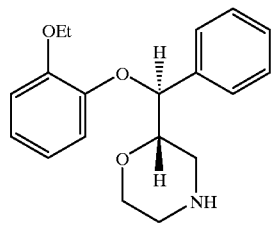

7. The method of claim 5 further comprising:

h) reacting the methane sulfonate salt with chloroacetyl chloride to give an amide of formula VIII:

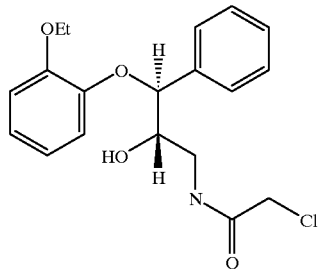

VIII i) reacting the compound of formula VIII to give a compound of formula IX:

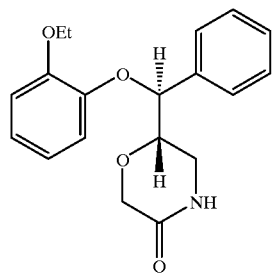

IX and j) reducing the compound of formula IX to give a corresponding morpholine compound of the following formula:

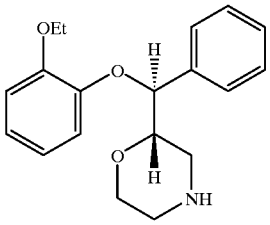

8. The method of claim 6 or 7 further comprising forming a pharmaceutically acceptable salt of the morpholine compound.

9. The method of claim 8 wherein the salt is a methane sulfonate salt.

* * * * *

UNITED STATES PATENT AND TRADEMARK OFFICE
CERTIFICATE OF CORRECTION

PATENT NO. : 6,376,711 B1  
DATED : April 23, 2002  
INVENTOR(S) : Kevin E. Henegar, Sarah E. Mancini and Keith D. Maisto It is certified that error appears in the above-identified patent and that said Letters Patent is hereby corrected as shown below:

<u>Title page,</u>
Item [56], References Cited, OTHER PUBLICATIONS, delete "vol." and insert
-- Vol. --, therefor.

<u>Column 28,</u>
Line 65, delete "VII:" and insert -- VIII: --, therefor.

Signed and Sealed this

Twenty-sixth Day of November, 2002

Attest:

Attesting Officer

JAMES E. ROGAN
*Director of the United States Patent and Trademark Office*